United States Patent
Shukla et al.

(10) Patent No.: US 6,618,613 B1
(45) Date of Patent: Sep. 9, 2003

(54) NON-AXIAL BODY COMPUTED TOMOGRAPHY

(75) Inventors: Himanshu P. Shukla, Gates Mills, OH (US); James R. Rauchut, Ivyland, PA (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 09/864,575

(22) Filed: May 24, 2001

(51) Int. Cl.[7] .............................................. A61B 5/00
(52) U.S. Cl. ...................... 600/425; 378/20; 378/208; 378/209; 5/601
(58) Field of Search ................ 600/425, 415; 378/17, 208, 209, 4, 20; 5/601

(56) References Cited

U.S. PATENT DOCUMENTS

| | | | | |
|---|---|---|---|---|
| 4,961,208 A | * | 10/1990 | Okada | 378/17 |
| 4,984,774 A | | 1/1991 | Zupancic et al. | 269/322 |
| 5,042,487 A | * | 8/1991 | Marquardt | 600/425 |
| 5,119,408 A | | 6/1992 | Little et al. | 378/4 |
| 6,385,481 B2 | * | 5/2002 | Nose et al. | 600/415 |
| 6,400,791 B1 | * | 6/2002 | Schwarz | 378/17 |

FOREIGN PATENT DOCUMENTS

EP   0 931 505 A2   7/1999

OTHER PUBLICATIONS

Horiguchi, et al. "Utility of Thin–section/High–pitch Helical CT for the Assessment of Small Lung Nodules" Nippon Acta Radiologica 1999; 59:53–59.

Caldemeyer, et al. "Temporal Bone: Comparison of Isotropic Helical CT and Conventional Direct Axial and Coronal CT", AJR 1999; 172:1675–1682.

Venema, et al. "Petrosal Bone: Coronal Reconstructions from Axial Spiral CT Data Obtained with 0.5–mm Collimation Can Replace Direct Coronal Sequential CT Scans", Radiology 1999; 213:375–382.

Eibel, et al., "Bildanalyse bei der Mehrschicht–Spiral –CT der Lunge mit MPR–und MIP–Rekonstruktionen", Radiolonge 1999; 39:952–957.

Wong et al. "Clinical and Computed Tomographic Features of Tracheal Bronchus in Children", J Formos Med Assoc 1999; V. 98, No. 9, 646–648.

* cited by examiner

Primary Examiner—Ruth S. Smith
(74) Attorney, Agent, or Firm—Fay, Sharpe, Fagan, Minnich & McKee, LLP

(57) ABSTRACT

In pediatric diagnostic imaging, a patient is seated upright on a patient couch (10) of a large bore CT scanner. The patient is seated such that coronal or near coronal slices are taken as opposed to axial slices as in typical CT scanners. The patient is stationarily supported in this position during imaging. A back support member (14) supports the back and side restraint panels (18) limit lateral movement. Restraint straps (30) further secure selected parts of the patient. The angle of the support member (14) is adjusted to conform with a selected imaging region by angle adjustment grooves (20). A removable telescopic head rest (40) positions the patient leaning forward. The back support (14), the side restraint panels (18), and the headrest (40) are all constructed of radiolucent materials.

13 Claims, 2 Drawing Sheets

NON-AXIAL BODY COMPUTED TOMOGRAPHY

BACKGROUND OF THE INVENTION

The present invention relates to the diagnostic imaging arts. It finds particular application in non-axial pediatric diagnosis using computed-tomography (CT) and will be described with particular reference thereto. However, it is to be appreciated that it is also applicable to non-pediatric applications and imaging scenarios, and is not limited to the aforementioned applications.

In a slice mode, CT scanners procure image data by taking a plurality of contiguous slices of a subject and reconstructing them into a volumetric representation. Typically this is done by taking axial or near axial slices, that is, taking slices that are substantially perpendicular to a longitudinal (head to toe) axis of a subject.

In a spiral mode, volume images are collected by moving the x-ray beam through a spiral trajectory around the longitudinal axis. Commonly, the source rotates continuously while the patient support moves longitudinally back and forth.

A limitation of present devices is that patients are inserted head-first or feet-first. Often, only a few slices along a major axis of an organ or tissue of interest are necessary. Organs and anatomical structures that have large longitudinal profiles such as the spine or lungs require many axial slices to generate a single longitudinal slice.

The generation of numerous axial slices is time consuming, plus penetrating radiation can be harmful to living cells. Not only is the tissue in the longitudinal slice of interest irradiated, all tissue in the axial planes around the longitudinal slice of interest are irradiated from many directions. In particular, cells that divide rapidly are more susceptible to radiation than slower dividing cells. In general, children are more susceptible to radiation damage than adults simply because they are growing and their cells are dividing faster. When using penetrating radiation to image children, it is desired to keep the dosage as low as possible and limit the irradiation, as much as possible, to the specific slices to be displayed. In addition, children tend to be more restless than adults. Thus, motion artifacts become problematic, especially in temporally longer scans. A more efficient method of imaging portions of the body with large axial profiles which lessens exposure and scan time is desirable.

Another problem with imaging children is that an attendant frequently remains close at hand to assist in keeping the child still, as well as to comfort the child. Although the attendant does not enter the imaging region, she still receives a nominal amount of scattered radiation. Over many scans of many different children, the received dosages of the attendant becomes problematic.

The present invention provides a new and improved method and apparatus that overcomes the above referenced problems and others.

SUMMARY OF THE INVENTION

In accordance with one aspect of the present invention, a computed tomography apparatus is given. Radiation from a source is detected by an array of detectors and reconstructed into an image representation of a patient within the apparatus. A patient support that provides support for the patient in a seated position within the apparatus is located on a patient couch.

In accordance with another aspect of the present invention, a method of diagnostic imageing is given. A subject is positioned in a seated position within an imaging region of a CT scanner. A source emits radiation into the region and is detected after it traverses the region. The detected radiation is converted into corresponding electronic data and reconstructed into an image representation.

In accordance with another aspect of the present invention, a patient seat for use in conjunction with a third or fourth generation CT scanner is given. A back support that supports an upper torso of a patient in an upright position rests upon a base portion that supports the weight of a patient. The base portion and back support fit inside a bore of the CT scanner.

One of the advantages of the present invention resides in shorter scan times.

Another advantage resides in less received dose by the patient.

Another advantage resides in improved image quality.

Yet another advantage resides in the ability to procure non-axial image slices.

Still further benefits and advantages of the present invention will become apparent to those skilled in the art upon a reading and understanding of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENT

Figure 1:
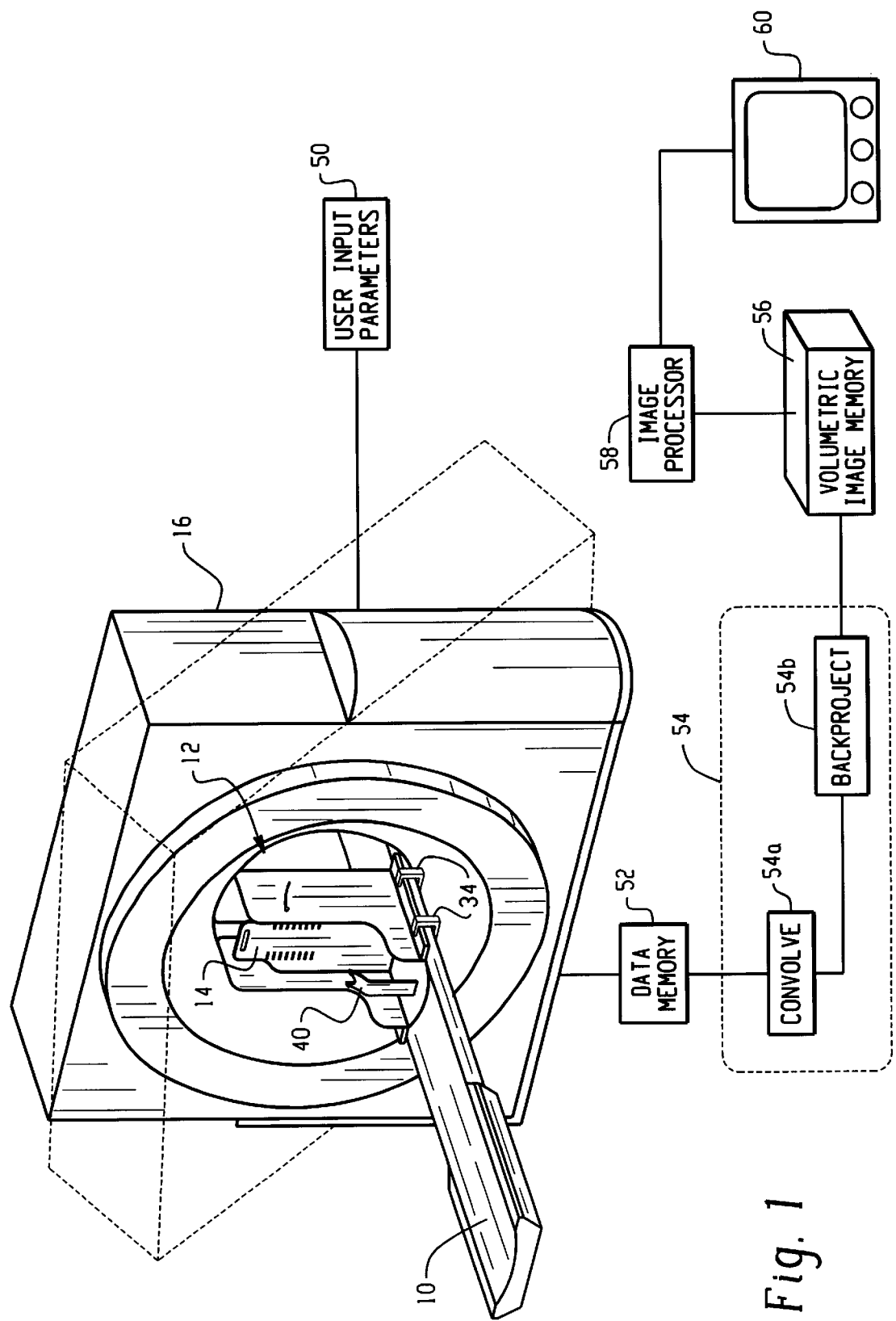
FIG. 1 is a diagrammatic illustration of a CT scanner an patient support in accordance with the present invention.

With reference to FIG. 1, a mobile patient couch 10 is disposed adjacent an aperture 12 of a computed tomography scanner. In the preferred embodiment, the aperture 12 is approximately 85 cm, larger than those of typical present day CT scanners. Optionally, smaller apertures such as 75 cm, are practical. Preferably, the CT scanner is a third or fourth generation machine. An x-ray source, disposed on a perimeter of the aperture 12 emits a fan or cone of x-rays into an imaging region. In a third generation machine, an array of detectors is disposed opposite to and rotates with the x-ray source to detect the radiation. The array moves in synchronization with the source, such that the center of the array is 180° around the perimeter from the source. In a fourth generation machine, the perimeter is lined with stationary detectors, and the source rotates about the perimeter.

In the preferred embodiment, a patient support and positioner 14 is supported on the patient couch 10. The support 14 fits into the aperture 12 of a CT scanner gantry 16. A large aperture 12 yields several advantages. One is that the patient feels less cramped, helping the patient relax. Another advantage is that it allows patients to sit upright or other non-prone positions during scans, as opposed to only lying flat.

The patient support and positioner 14 provides stability and secure stationary support for a child or small adult in a seated or other selected, non-axial imaging position on the patient couch 10. Taller patients are supportable in partially reclined positions. With the patient in this position, coronal, and sagittal slices of the patient are collected.

In particular applications, organs and other bodily structures are imaged that are longitudinally elongated but have relatively small transverse profiles. Some examples are the lungs, spinal column, and kidneys. While it would take many slices to image the entire spinal column with axial slices, it takes but a few slices with a coronal orientation. By positioning the patient seated with the spine vertical, the coronal plane through the spine can be aligned with the plane of rotation of the x-ray beam. Coronal imaging captures the spine with only a few slices. Therefore, less of the body receives useless radiation. Moreover, the eyes and other radiation sensitive organs are positioned outside of the x-ray beam during data acquisition.

Figure 2:
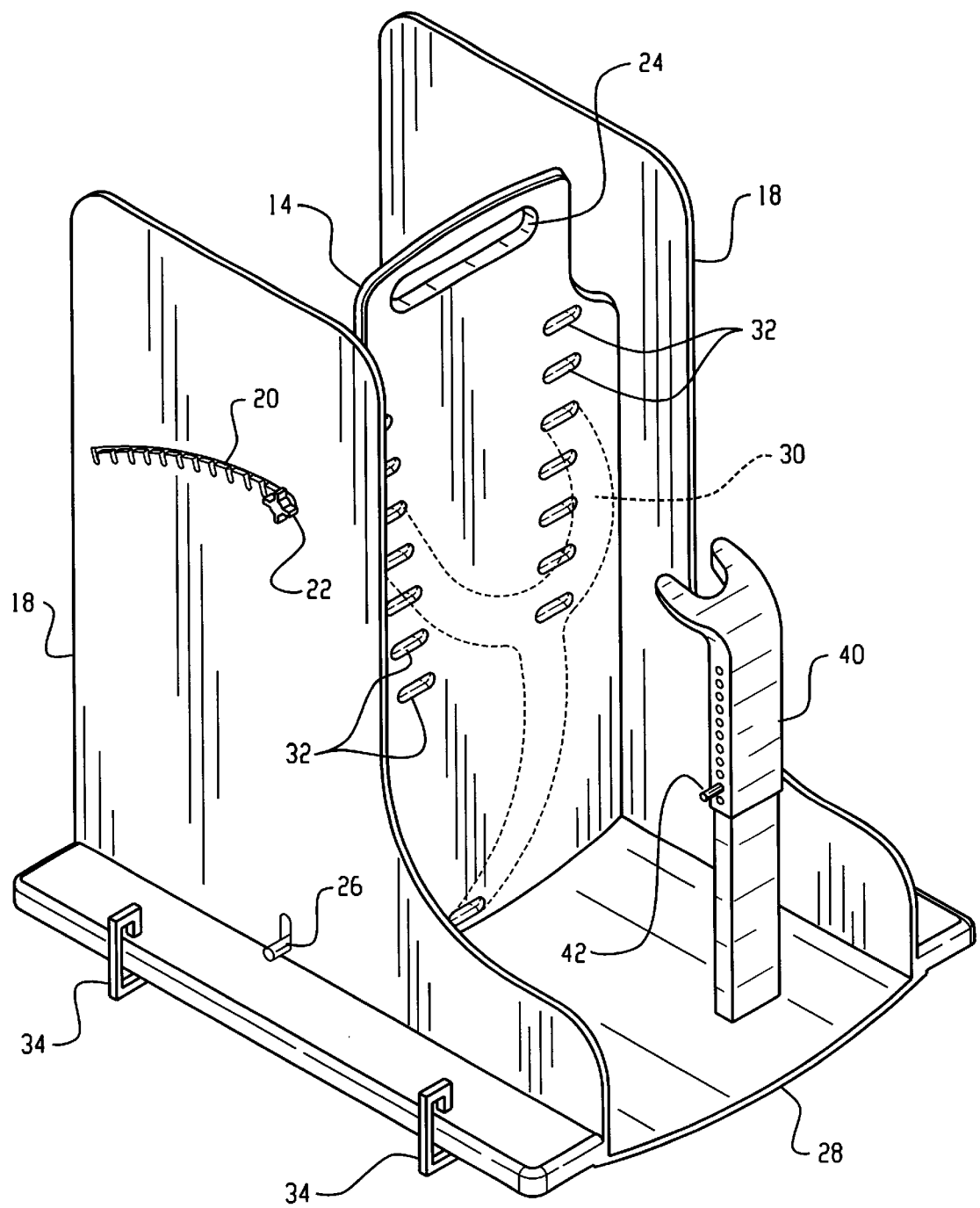
FIG. 2 is a perspective view of the patient support.

With reference to FIG. 2 and continuing reference to FIG. 1, the back support member 14 of the preferred embodiment is flanked by two side restraint panels 18. The restraint panels have matching angle adjustment grooves 20 for an attendant or operator to select an angle of the back support member 14 with respect to a vertical axis. Thus, varying entry orientations can be achieved by manipulating the angle of the support member. To do this, the operator loosens two securing knobs 22 one on each side of the support member 14. The operator grasps the support member 14 by a handle 24 or by the knobs 22 and lifts it from the angle adjustment grooves 20. Pivot pins 26 received in elongated slots allow the support member 14 to be lifted sufficiently for the knobs 22 to clear the grooves 20. The back support is tilted within the range of the adjustment grooves 20. The operator lifts the back support 14, selects one of the grooves 20 corresponding to a selected tilt, and lowers the support member 14 until the knobs are received in the selected groove. The knobs are tightened to help prevent the support member from shifting during an imaging process. In addition, the angle of the irradiated slice is varied by tilting the gantry 16, as ghosted in FIG. 1.

The side restraint panels 18 also serve as rigid restraints against lateral movement during imaging. As children tend to become restless when uncomfortable or nervous, the restraint panels 18 remind and arrest the child to remain still. Additional restraints, such as straps 30 with Velcro™ hook an loop connectors, a harness, or the like extend from the support member. The support member 14 is equipped with multiple strap holes 32 for securing the restraint straps 30. A wide range of patient heights are accommodated. The operator chooses among the plurality of strap holes 32 to select ones that best fit the patient height or desired position in the apparatus. Additional supports and restraints such as foam wedges or cushions are contemplated.

In addition to improving image quality by reducing motion artifacts, the restraints also allow for less attendant interaction. While an attendant may remain in the room, the attendant will not remain as close to the CT scanner to attend to the child when the machine is in operation. The attendant may also wear more mobility constricting radiation shielding garments.

The base board 28 defines a seat where the patient sits during imaging. The base board 28 is temporarily attachable to the patient couch. The base board 28 has a convex shape that matches the concave shape of the patient couch 10. The base board 28 is attached to the patient couch with radiolucent clamps 34, straps, or other configurations that are designed to engage the couch When the base board 28 is positioned and secured to the couch 10 for coronal imaging, the assembly is oriented such that the legs of the patient extend along the patient couch. During a slice imaging sequence, the back support and gantry are angled and the couch is moved longitudinally to align a slice of interest with the plane of the radiation beam. For spiral, volume imaging, the couch 10 translates into and out of the aperture 12 while the x-ray source is rotating.

Alternately, the base board 28 can be shaped such that it fits 90° rotated from the orientation previously described. This orientation facilitates sagittal imaging of the subject.

In the preferred embodiment, the back support member 14, the side restraint panels 18, the base board 22, and the restraint straps 30 are all made of carbon fiber reinforced polymers, low density wood, or other radiolucent material which does not contribute negatively to the imaging process.

In the preferred embodiment, a removable telescopic head rest 40 is used for certain imaging procedures. The head rest is adjustable to varying heights. A height adjustment pin 42 is used to select the height of the headrest 40 depending on the size of the patient, desired position, etc. Varying heights are selected by removing the adjustment pin 42 sliding the upper section up or down on the lower section and reinserting the pin in a different hole. The headrest 40 is also removable entirely if it is not required. The upper section is shaped to receive the patient's forehead when it is desired to keep the head of the patient out of the scan region. The eyes, for example, are especially sensitive to the x-rays. Sometimes procedures are performed in which uncomfortable or contorted positions are held for the duration of the scan. The head rest 40 helps make such positions more bearable by providing a soft support for the head of the patient.

With further reference to FIG. 1, prior to the patient being inserted into the machine, the operator submits selected parameters 50 into the machine. Parameters such as slice thickness, number of slices, gantry tilt angle, scanning mode, and the like are selected. After the patient is disposed on the patient couch 10 in the selected position, the operator initiates the selected procedure. The source rotates around the gantry 16 emitting x-rays which are detected by the detectors opposite the source. The views of the x-ray detectors are stored in a pre-reconstruction data memory or buffer 52. The view data is reconstructed in a reconstruction processor 54. In an exemplary reconstruction, the views are convolved 54a and backprojected 54b to form a slice image. For a volume image, a plurality of slices are then reconstructed and stacked in a volumetric image memory 56. Spiral and other reconstruction techniques are also contemplated. The operator then selects desired portions of the volume for viewing. An image processor 58 formats slice images, 3D renderings, and the like for display on a human readable display 60 such as a video monitor, liquid crystal display, active matrix monitor, or the like.

In an alternate embodiment, a cine mode is available. This mode is applicable to dynamic temporal scanning techniques. The x-ray source rotates about one slice or a small number of slices. Images are continuously reconstructed and viewed as new ones become available. In this manner, real time, or semi-real time images of the subject are acquired. Some possible applications are bolus tracking, digestive/respiratory tract studies, joint movement, etc.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A computed tomography apparatus comprising:
a gantry defining a vertical aperture for receiving a patient;
at least one source of penetrating radiation mounted in the gantry for rotation about the aperture in a substantially vertical plane;
an array of detectors for detecting the penetrating radiation mounted in the gantry;
a patient couch extending horizontally into the aperture for transporting the patient into the aperture along a horizontal path;
a patient support that supports the patient in a seated position inside the aperture of the gantry on the patient couch with an upper body of the patient oriented substantially vertically;
a reconstruction processor that reconstructs multiple views of sagittal slices of the patient upper body into an image representation.

2. The computed tomography apparatus as set forth in claim 1, wherein a diameter of the gantry aperture is at least 75 cm.

3. A computed tomography apparatus comprising:
a source of penetrating radiation which rotates in an imaging plane around an imaging region;
radiation detectors positioned across the imaging region from the radiation source in the imaging plane;
a patient couch which has a patient supporting surface extending transverse to the imaging plane and adapted to convey a patient longitudinally through the imaging plane;
a patient support removeably positioned on the patient supporting surface to support a patient in a seated position on the patient couch, the patient support including:
a base removeably supported on the patient couch patient supporting surface;
a back support connected with the base for supporting a patient's back in the seated position with the sagittal plane substantially parallel to the imaging plane.

4. The computed tomography apparatus as set forth in claim 3, wherein the patient support further includes:
an angle adjustment mechanism for adjusting an angle of the back support relative to the base.

5. The computed tomography apparatus as set forth in claim 4, wherein the patient support further includes:
side members connected with the base and disposed along opposite sides of the back support.

6. The computed tomography apparatus as set forth in claim 3, wherein the patient support further includes:
restraint devices for restricting movement of the subject during an imaging process.

7. The computed tomography apparatus as set forth in claim 3, wherein the patient support further includes:
a headrest positioned to support a head of the patient displaced from the imaging plane.

8. A computed tomography apparatus comprising:
a gantry defining an aperture for receiving a patient;
at least one source of penetrating radiation mounted for rotation about the aperture;
an array of detectors for detecting the penetrating radiation which has traversed the aperture;
a patient couch;
a patient support that supports the patient in a seated position inside the aperture of the gantry on the patient couch, the patient support including:
a base, configured to be supported on the patient couch,
a back support connected with the base for supporting a patient's back in the seated position,
side members connected with the base and disposed along opposite sides of the back support,
an angle adjustment mechanism for adjusting an angle of the back support relative to the base, the angle adjustment mechanism including:
a pivot which pivotally connects the back support to the side members;
an arcuate guide with a series of grooves extending radially of the pivot for defining a plurality of selectable tilt angles;
a reconstruction processor that reconstructs multiple views of the patient into an image representation.

9. A computed tomography device comprising:
a gantry defining an aperture for receiving a patient;
at least one source of penetrating radiation mounted in the gantry for rotation about the aperture;
an array of detectors for detecting the penetrating radiation from the source which has traversed on imaging plane;
a patient couch;
a patient support that supports the patient in a seated position inside the aperture of the gantry on the patient couch, the patient support further including:
a supplementary patient supports that supports a sagittal plane of the patient in and parallel to the imaging plane;
a reconstruction processor that reconstructs multiple views of the patient into an image representation.

10. A method of diagnostic imaging comprising:
positioning a subject in a seated position in an imaging region of a CT scanner with a sagittal plane of the subject's torso disposed substantially vertically;
rotating a source of radiation around the imaging region in a substantially vertical plane;
detecting radiation from the source that has traversed the imaging region and generating corresponding electronic data; and,
reconstructing the electronic data into an image representation.

11. The method as set forth in claim 10, further including:
selecting an angle of the subject's upper torso relative to a vertical axis;
selecting an angle of a plane within which the radiation source rotates relative to the vertical axis.

12. The method as set forth in claim 11, further including:
positioning a head of the subject out of the radiation source rotation plane.

13. A method of diagnostic imaging comprising:
positioning a subject in a seated position in an imaging region of a CT scanner with the subject's upper torso parallel to a radiation source rotation plane;
rotating a source of radiation around the imaging region in the source rotation plane;
detecting radiation from the source that has traversed the imaging region and generating corresponding electronic data; and,
reconstructing the electronic data into an image representation.

* * * * *